United States Patent [19]

Kilbane II

[11] Patent Number: 5,198,341
[45] Date of Patent: Mar. 30, 1993

[54] USEFUL FOR CLEAVAGE OF ORGANIC C-S BONDS BACILLUS SPHAERICUS MICROORGANISM

[75] Inventor: John J. Kilbane II, Woodstock, Ill.

[73] Assignee: Institute of Gas Technology, Chicago, Ill.

[21] Appl. No.: 640,931

[22] Filed: Jan. 14, 1991

Related U.S. Application Data

[63] Continuation of Ser. No. 461,265, Jan. 5, 1990, Pat. No. 5,002,888.

[51] Int. Cl.$^5$ .................. C12P 11/00; C12R 1/07; C12R 1/125; C10G 32/00
[52] U.S. Cl. .................. 435/42; 435/130; 435/156; 435/166; 435/168; 435/252.31; 435/252.4; 435/252.5; 435/281; 435/282; 435/832
[58] Field of Search .................. 435/42, 252.31, 130, 435/156, 166, 168, 252.4, 252.5, 832, 281, 282

[56] References Cited

U.S. PATENT DOCUMENTS

| | | |
|---|---|---|
| 2,641,564 | 6/1953 | Zobell . |
| 4,055,468 | 10/1977 | Umezawa et al. . |
| 4,206,288 | 6/1980 | Detz et al. . |
| 4,562,156 | 12/1985 | Isbister et al. . |
| 4,632,906 | 12/1986 | Kopacz . |
| 4,659,670 | 4/1987 | Stevens, Jr. et al. . |
| 4,808,535 | 2/1989 | Isbister . |
| 5,002,888 | 3/1991 | Kilbane ................ 435/42 |
| 5,132,219 | 7/1992 | Kilbane ................ 435/252.31 |

OTHER PUBLICATIONS

Sorkhoh, N. A., et al., "Crude Oil and Hydrocarbon-Degrading Strains of Rhodococcus Rhodochrous Isolated from Soil and Marine Environments in Kuwait", *Environmental Pollution*, 65, 1990, pp. 1–17.
Bauch, J., Gentzsch, H., Hieke W., Eckart, V., Koehler, M., and Babenzin, H. D., "Oxidative Microbiological Desulfurization of Heavy Petroleum Fractions", Chemical Abstracts, vol. 83, No. 82530y (1975).
Eckart, V., Hieke, W., Bauch, J., and Gentzsch, H., "Microbial Desulfurization of Petroleum and Heavy Petroleum Fractions. 1. Studies on Microbial Aerobic Desulfurization of Romashkino Crude Oil", Chemical Abstracts, vol. 94, No. 142230q (1981).
Eckart, V., Hieke, W. Bauch, J., and Gentzsch, H., "Microbial Desulfurization of Petroleum and Heavy Petroleum Fractions, 3, Change in the Chemical Composition of Fuel-D-Oil by Microbial Aerobic Desulfurization", Chemical Abstracts, vol. 97, No. 147259c (1982).
Eligwe, C. A., "Microbial Desulfurization of Coal", Fuel, 67:451–458 (1988).
Hartdegen, F. J., Coburn, J. M., and Roberts, R. L., "Microbial Desulfurization of Petroleum", Chem. Eng. Progress, vol. 80, No. 5, pp. 63–67 (1984).
Hou, C. T. and Laskin, A. I., "Microbial Conversion of Dibenzothiophene", *Dev. Ind. Microbiol.*, 17, 351–362 (1976).
Isbister, J. D. and Kobylinski, E. A., "Microbial Desulfurization of Coal in Processing and Utilization of High Sulfur Coals", Coal Science and Technology Series, No. 9, 627, Attia, Y. A., Ed., Amsterdam: Elsevier (1985).
Kargi, F. and Robinson, J. M., "Microbial Oxidation of Dibenzothiophene by the Thermophilic Organisms Sulfolobus acidocaldarius", Biotech. and Bioeng., 126, 687–690 (1984).
Kilbane, John J., "Sulfur-Specific Microbial Metabolism of Organic Compounds", Bioprocessing of Coals Workshop, Tysons Corner, Va., Aug. 16–18, 1988.
Kodama, K. Nakatani, S., Umehara, K., Shimizu, K., Minoda, Y., and Yamada, K., "Microbial Conversion of Petrosulfur Compounds: Isolation and Identification of Products from Dibenzothiophene", Agr. Biolog. Chem., 34, 1320–1324 (1970).
Laborde, A. L., and Gibson, D. T., "Metabolism of Dibenzothiophene by a Beijerinckia Species", *Appl. Environ. Microbiol.* 34, 783–790 (1977).
Lee, Min Jai and Oh, Myung Soo, "Isolation, Identification, and Physiological Characteristics of some Sulfur-Reducing Microbes", Chemical Abstracts, vol. 78, No. 94605m (1973).
Lee, M. J., Hah, Y. C., and Lee, K. W., "Desulfurization of Petroleum by Microorganisms. I. Isolation and Identification of Sulfur-Oxidizing and —Reducing bacteria", Chemical Abstracts, vol. 85, No. 156414d (1976).
Lee, M. J., Hah, Y. C., and Lee, K. W., "Desulfurization of Petroleum by Microorganisms. III. Desulfurization of Petroleum by Contact Reaction with Desulfurizing Bacteria", Chemical Abstracts, vol. 85, No. 145448s (1976).
Malik, K. A., "Microbial removal of Organic Sulfur from Crude Oil and the Environment: Some New Perspectives", *Process Biochem.*, 13(9), 10–13 (1978).
Monticello, D. J., Bakker, D., and Finnerty, W. R., "Plasmid Mediated Degradation of Dibenzothiophene by *Pseudomonas* Species", *Appl. Environ. Microbiol.*, 49, 756–760 (1985).
Yuda, Sadayuki, "Petroleum Desulfurization by *Pseudomonas haconensis*", Chemical Abstracts, vol. 84, No. 46982j (1976).
Knecht, A. T., Jr., "Microbial Oxidation of Dibenzothiophene and Its Possible Application in the Desulfurization of Coal and Petroleum", Thesis Dissertation, Louisiana State University, 1961.

*Primary Examiner*—Herbert J. Lilling
*Attorney, Agent, or Firm*—Speckman & Pauley

[57] ABSTRACT

A mutant *Bacillus sphaericus* strain ATCC No. 53969 which has the property of sulfur removal and sulfur metabolism by selective cleavage of C-S bonds in organic carbonaceous materials.

22 Claims, No Drawings

USEFUL FOR CLEAVAGE OF ORGANIC C-S BONDS BACILLUS SPHAERICUS MICROORGANISM

The U.S. Government has rights in this invention as set forth in Department of Energy Contract No. DE-AC22-85PC81201.

CROSS REFERENCE TO RELATED APPLICATION

This application is a continuation application of co-pending application Ser. No. 07/461,265, filed Jan. 5, 1990, now U.S. Pat. No. 5,002,888.

BACKGROUND OF THE INVENTION

1. Field of the Invention

This invention relates to a mutant strain of *Bacillus sphaericus* capable of selective removal of organically bound sulfur from carbonaceous materials while maintaining the calorific value of the carbonaceous materials. The microorganisms of this invention are particularly useful in removal of organic sulfur from fossil fuels such as sulfur-containing coal and oils.

2. Description of the Prior Art

Sulfur content of carbonaceous fuels, such as coals and oils, has prevented utilization of a considerable amount of such materials due to deleterious effect upon the environment. Inorganic pyritic sulfur and organically bound sulfur ma each constitute as much as about 3.5 weight percent of the coal. Pyritic sulfur has been found to be relatively easy to remove by techniques including heavy media separation, selective agglomeration, flotation, jigging, magnetic separation, leaching and hydrosulfurization. Microbial metabolism of inorganic pyritic sulfur by its oxidation using bacteria such as Thiobacillus and Sulfolobus species is known. Eligwe, C. A., "Microbial Desulfurization of Coal," Fuel, 67:451–458 (1988). These chemolithotropic organisms can utilize inorganic pyritic sulfur compounds as energy sources and are capable of removing 90% or more of the inorganic pyritic sulfur from coal within a few days. *Thiobacillus ferrooxidans* is taught by U.S. Pat. No. 4,206,288 as suitable for removal of pyritic sulfur from coal.

*Bacillus sulfasportare* ATCC 39909 has been taught by U.S. Pat. No. 4,632,906 to be capable of sulfur removal from coal, without differentiation between pyritic and organic sulfur. An unidentified mixed culture of seven gram negative rods (ATCC 39327) prepared by growth in situ enriched with sulfur compounds and subsequently grown in the presence of coal has been shown to reduce the sulfur content of coal by about 20 percent per day with a substantial portion being reduction of organic sulfur as taught by U.S. Pat. No. 4,659,670.

Removal of sulfur from petroleum hydrocarbons by contact with hydrogen in the presence of hydrogenase-producing microorganisms *Desulfovibrio desulfuricans* and Sporovibrio followed by removal of sulfur in the form of gaseous products is taught by U.S. Pat. No. 2,641,564. Removal of sulfur from petroleum by Pseudomonas is taught by Hartdegen, F. J., Coburn, J. M., and Roberts, R. L., "Microbial Desulfurization of Petroleum," Chem. Eng. Progress, Vol. 80, No. 5, pp. 63–67 (1984) to be by C-C cleavage. General teachings of various Pseudomonas for removal of sulfur from petroleum are in Eckart, V., Hieke, W., Bauch., J., and Gentzsch, H., "Microbial Desulfurization of Petroleum and Heavy Petroleum Fractions. 1. Studies on Microbial Aerobic Desulfurization of Romashkino Crude Oil," Chemical Abstracts, Vol. 94, No. 142230q, (1981); Eckart, V., Hieke, W., Bauch, J., and Gentzsch, H., "Microbial Desulfurization of Petroleum and Heavy Petroleum Fractions. 3. Change in the Chemical Composition of Fuel-D-Oil by Microbial Aerobic Desulfurization," Chemical Abstracts, Vol. 97, No. 147259c, (1982); Lee, Min Jai and Oh, Myung Soo, "Isolation, Identification, and Physiological Characteristics of Some Sulfur-Reducing Microbes," Chemical Abstracts, Vol. 78, No. 94605m (1973); Bauch, J., Gentzsch, H., Hieke, W., Eckart, V., Koehler, M., and Babenzin, H. D., "Oxidative Microbiological Desulfurization of Heavy Petroleum Fractions," Chemical Abstracts, Vol. 83, No. 82530y (1975); and Yuda, Sadayuki, "Petroleum Desulfurization by *Pseudomonas haconensis,*" Chemical Abstracts, Vol. 84, No. 46982j (1976). *Thiobacillus thiooxidans* has been identified as the most effective S-oxidizer and *Pseudomonas putrefaciens* and *Desulfovibrio desulfuricans* the most effective S-reducers in microbial removal of sulfur from petroleum, Lee, M. J., Hah, Y. C., and Lee, K. W., "Desulfurization of Petroleum by Microorganisms. I. Isolation and Identification of Sulfur-Oxidizing and - Reducing Bacteria," Chemical Abstracts, Vol. 85, No. 156414d (1976); Lee, M. J., Hah, Y. C., and Lee, K. W., "Desulfurization of Petroleum by Microorganisms. III. Desulfurization of Petroleum by Contact Reaction with Desulfurizing Bacteria," Chemical Abstracts, Vol. 85, No. 145448s (1976).

Organic sulfur which is chemically bound within the carbonaceous molecule must be removed either by chemical or biological means. Dibenzothiophene (DBT) is the organosulfur compound most persons consider representative of the form in which organic sulfur exists in naturally occurring organic carbonaceous fuels such as coal and oil and is the compound upon which the microbial metabolism of organosulfur compounds has focused. Study of DBT metabolism has been pursued by several researchers who have isolated organisms capable of metabolizing DBT including Acinetobacter, Malik, K. A., "Microbial Removal of Organic Sulfur from Crude Oil and the Environment: Some New Perspectives," Process Biochem., 13(9), 10–13 (1978); Arthrobacter, Knecht, A. T., Jr., Thesis Dissertation, Louisiana State University, Order No. 621235 (1961); Beijerinckia, Laborde, A. L., and Gibson, D. T., "Metabolism of Dibenzothiophene by a Beijerinckia Species," Appl. Environ. Microbiol., 34, 783–790 (1977); Rhizobium, Malik, K. A., (supra); Pseudomonas, Hou, C. T. and Laskin, A. I., "Microbial Conversion of Dibenzothiophene," Dev. Ind. Microbiol., 17, 351–362 (1976); Isbister, J. D. and Kobylinski, E. A., "Microbial Desulfurization of Coal in Processing and Utilization of High Sulfur Coals," Coal Science and Technology Series, No. 9, 627, Attia, Y. A., Ed. Amsterdam: Elsevier (1985); Knecht, A. T., Jr., (supra); Kodama, K., Nakatani, S., Umehara, K., Shimizu, K., Minoda, Y., and Yamada, K., "Microbial Conversion of Petrosulfur Compounds: Isolation and Identification of Products from Dibenzothiophene," Agr. Biolog. Chem., 34, 1320–1324 (1970); Monticello, D. J., Bakker, D., and Finnerty, W. R., "Plasmid Mediated Degradation of Dibenzothiophene by Pseudomonas Species," Appl. Environ. Microbiol., 49, 756–760 (1985); Sulfolobus, Kargi, F. and Robinson, J. M., "Microbial Oxidation of Dibenzothiophene by the Thermophilic Organisms *Sulfolobus acidocaldarius,*" Biotech.

and Bioeng., 126, 687-690 (1984). The pathway of microbial degradation of DBT in each of the above cases except in Isbister, et al., (supra), is by C-C bond cleavage according to microbial degradation pathways of DBT originally established by Kodama, et al., (supra). Microbial degradation of organic sulfur-containing carbonaceous materials by C-C bond cleavage results in the loss of a large portion of the calorific value of the carbonaceous fuel. According to the Kodama, et al. (supra), C-C bond cleavage microbial degradation of DBT, sulfur-containing end products are 3-hydroxybenzothiophene sulfoxide, 2-formyl benzothiophene, or benzothiophene. It is, therefore, desirable to follow a microbial degradation route which removes sulfur from the molecule without removing carbon from the molecule, thereby retaining calorific value of the fuel to a greater degree than is possible by carbon degradative pathways. Such sulfur-specific metabolism of the organic substrates requires cleavage of carbon-sulfur bonds in the organic sulfur-containing molecule. In the case of sulfur specific metabolism of dibenzothiophene, the end products are 2-hydroxybiphenyl and

This C-S cleavage pathway is believed to proceed according to dibenzothiophene→dibenzothiophene sulfoxide dibenzothiophene sulfone→dibenzothiophene sulfonate→2-hydroxybiphenyl+inorganic sulfate. The monohydroxy product of this C-S cleavage route distinguishes it from routes leading to significant amounts of bihydroxybiphenyl.

The only prior microorganism known to the present inventor allegedly capable of degradation of DBT by C-S cleavage is a Pseudomonas species as described by Isbister, (supra), and Pseudomonas ATCC 39381, as set forth in U.S. Pat. No. 4,562,156. The ATCC 39381 culture on deposit does not possess the C-S cleavage trait and the depositors of the culture have stated that the culture on deposit cannot be replaced as such cultures having the C-S cleavage trait to their knowledge do not exist. (4th Department of Energy Preparation, Utilization and Environmental Control Contractors Conference, U.S. Dept. of Energy, Pittsburgh Energy Technology Center, Pittsburgh, Pa. 15236, U.S.A., 1988). Mixed cultures obtained through growth under sulfur limited conditions have been capable of selective removal of sulfur from DBT, Kilbane, John J., "Sulfur-Specific Microbial Metabolism of Organic Compounds," Bioprocessing of Coals Workshop, Tysons Corner, Va., Aug. 16-18, 1988.

SUMMARY OF THE INVENTION

It is an object of this invention to provide a microorganism and a process for removal of organically bound sulfur from sulfur-containing organic carbonaceous materials.

It is another object of this invention to provide a microorganism and process for selective sulfur removal from organic sulfur-containing fossil and fossil derived fuels.

It is yet another object of this invention to provide a microorganism and process capable of specific cleavage of C-S bonds in reactions of organic carbonaceous materials, such as in organic synthesis and in recycling operations, such as recycling of rubber products.

It is still another object of this invention to provide a microorganism which is stable and retains its sulfur specific characteristics under process conditions using the microorganism for cleavage of organic C-S bonding.

It is another object of this invention to provide a microorganism and process for specific sulfur removal from dibenzothiophene resulting in substantially sole products of inorganic sulfate and 2-hydroxybiphenyl.

The above and other objects and advantages, as will become evident from reading of this description, have been achieved by the biologically pure culture of a mutant microorganism which has been produced, identified, and subjected to processes as set forth in further detail and identified as *Bacillus sphaericus*. The culture has been deposited with American Type Culture Collection and assigned ATCC Number 53969.

*Bacillus sphaericus* ATCC No. 53969 may be prepared by inoculating with mixed bacteria derived from sites having present materials of C-S bonding desired to be cleaved a growth medium comprising mineral nutrients, an assimilable source of carbon, and in substantial absence of a sulfur-containing compound, except compounds having sulfur present only in C-S bonding of the type desired to be cleaved; growing the bacterial culture in the presence of a helper culture furnishing nutrients necessary for *Bacillus sphaericus* ATCC No. 53969 growth and oxygen at temperatures about 20° to about 34° C. and in the substantial absence of a sulfur-containing compound except compounds having sulfur present only in C-S bonding of the type desired to be cleaved for sufficient time to selectively produce *Bacillus sphaericus* ATCC No. 53969 which has the property of sulfur metabolism by selective cleavage of C-S bonds in organic carbonaceous materials. The helper culture provides nutrient requirements for the *Bacillus sphaericus* ATCC No. 53969, but has no ability to metabolize organic sulfur.

Sulfur content of sulfur-containing organic carbonaceous material may be reduced by contacting such sulfur containing organic carbonaceous material with the microorganism *Bacillus sphaericus* strain ATCC No. 53969. The process is especially suitable for use where the sulfur-containing carbonaceous material is coal or hydrocarbon oil. Continuous growth of *Bacillus sphaericus* ATCC No. 53969 in the presence of sulfur-containing coal results in the removal of more than 80 percent, and preferably more than 90 percent, of the organically bound sulfur. The process for reducing the sulfur content of the sulfur-containing organic carbonaceous material occurs by cleavage of organic C-S bonds by the microorganism *Bacillus sphaericus* strain ATCC No. 53969. The organic sulfur selective mutant microorganism *Bacillus sphaericus* ATCC 53969 has the ability to selectively reduce the sulfur content of sulfur-containing organic carbonaceous material by cleavage of organic C-S bonds resulting in the production of inorganic sulfate when grown in a growth medium comprising a bacterial nutrient helper culture, mineral nutrients and an assimilable source of carbon in the substantial absence of a sulfur-containing compound except the sulfur-containing organic carbonaceous material, and in the presence of oxygen at temperatures about 20° to about 34° C. Derivative microorganisms of *Bacillus sphaericus* ATCC 53969 also have the ability to selectively reduce the sulfur content of sulfur-containing organic carbonaceous material by cleavage of organic C-S bonds in the same fashion.

DESCRIPTION OF PREFERRED EMBODIMENTS

Environmental cultures having a known history of exposure to organosulfur compounds as well as enrichment cultures using as carbon sources acetate, benzene, benzoic acid, ethanol, glucose, glycerol, nutrient broth, succinate, and toluene and organic sulfur compounds benzothiophene, dibenzothiophene, thiophene, trithiane, produced bacterial cultures capable of metabolizing each of the organic sulfur compounds used. All of the environmental isolates and enrichment cultures tested were found to metabolize organosulfur compounds by initiating biodegradation at the carbon-carbon bond except for a mixed culture enriched with thiophene as its sole source of sulfur which was shown to be capable of carbon-sulfur bond cleavage for about 20% of its products, the remaining 80% being the result of carbon-carbon bond cleavage. The most successful microorganism for sulfur utilization from organosulfur compounds was Pseudomonas isolated from enrichment cultures employing DBT as the sole source of sulfur. This Pseudomonas species while capable of utilizing organically bound sulfur failed to show specificity for the oxidation of carbon-sulfur bonds. This shows the failure of enrichment culture development of a naturally occurring microorganism showing specificity for oxidation of organic C-S bonds. Thus, an unnatural, selective mutation process must be utilized to develop a microorganism having such selective sulfur metabolism.

Microorganisms having sulfur-specific metabolic abilities with respect to organic substrates were developed by selection through a continuous culture coal bioreactor/selectostat in which nutrients and organically bound sulfur not normally found in living tissue may be supplied in the substantial absence of other available sulfur such as sulfates, vitamins, amino acids and the like. The growth media should supply organic and inorganic nutrients for good microorganism growth, but be devoid of inorganic and organic sulfur-containing compounds except those organic sulfur-containing compounds desired to be metabolized by the mutant microorganism. A suitable media for growth of microorganisms under organosulfur conditions may suitably be a composition of mineral nutrients, such as 4 gms $K_2HPO_4$, 4 gms $Na_2HPO_4$, 2 gms $NH_4Cl$, 0.2 gm $MgCl_2.6H_2O$, 0.001 gm $CaCl_2.2H_2O$, and 0.001 gm $FeCl_3.6H_2O$ per liter of distilled, deionized water. Any assimilable carbon source devoid of sulfur may be used in amounts to support desired microbial growth. Suitable assimilable carbon sources include glucose, glycerol, sodium acetate, sodium benzoate, sodium succinate, and sucrose at concentrations of about 20 mM and benzene, ethanol, isobutanol, and toluene may be used as vapors in the head space of the bacterial growth bioreactors. Organosulfur compounds having organic C-S bonds are suitable, including benzothiophene, benzyldisulfide, dibenzothiophene, dibenzothiophene sulfone, phenyldisulfide, thianthrene, thioxanthene (Aldrich Chemical Company, Milwaukee, Wis.), dibenzothiophene sulfoxide (ICN Biomedicals, K&K Labs, Plainview, N.J.) and trithiane (Faifield Chemical Company, P.O. Box 20, Clythewood, S.C.) may be used over concentration ranges which support microbial growth, in the order of about 20 mM and thiophene (Aldrich Chemical Company) may be used as a vapor. Nutrient broth (Difco Laboratories, Detroit, Mich.) or the above growth media solidified with about 15 g of agar (Difco) per liter may be employed for streaking or plating bacterial cultures. Bacterial growth may be monitored turbidimetrically using a Klett-Sommerson colorimeter or by enumerating colony forming units on appropriate agar.

Inoculum may be prepared by adding 5 gm samples of soil obtained from coal storage sites and from petroleum refinery sites to 10 ml of the above growth media, vortexed for 60 seconds, and allowed to settle for 30 minutes. The supernatants may be removed with a Pasteur pipette and used directly or diluted with an equal volume of nutrient broth and incubated at room temperature for about 24 to 48 hours before being used to inoculate the bioreactors.

Bioreactors/selectostats were of special design to provide continuous flow of liquid nutrients while retaining coal or organosulfur solids. The same batch of coal or organosulfur compound remains within the bioreactor for the duration of its operation whereas the aqueous phase media may be continuously supplied to the bioreactor. The retention of coal within the bioreactor for long periods of time may be accomplished by using relatively large particles of coal, typically $-9 +12$ mesh, and the use of an inclined, non-mixed sedimentation tube containing several weirs/baffles from which the bioreactor effluent may be withdrawn at relatively slow flow rates. The effluent withdrawal rates may be adjusted according to the ability of the microorganism to respond to the sulfur limitation challenge, typically, hydraulic retention times may be in the order of 72 hours.

The selectostats may be monitored frequently to determine suitable carbon source feed rate and to assay for presence of biologically available sulfur in the effluent. This may be achieved by centrifuging fresh bioreactor effluent to remove coal fines and particles of organosulfur substrate and bacteria followed by use of the supernatant in bacterial growth tests. Four cultures are prepared: the supernatant; the supernatant with 15 mM $SO_4$; a supernatant with 20 mM carbon source; and a supernatant with 15 mM $SO_4$ and 20 mM carbon source, each inoculated with a microbial culture at $10^5$ microorganism/ml and incubated for 2 to 5 days with shaking at growth temperatures for the microorganism being tested. Bacterial growth is monitored turbidimetrically or by determining colony-forming units. The carbon source sample serves to indicate the presence of biologically available sulfur in the effluent supernatant while the sample with added sulfate serves to indicate the presence of a carbon source in the effluent supernatant, and the sample containing both the carbon and added sulfate serves to indicate the presence of inhibitory substances in the effluent supernatant.

The ability of bacteria to utilize organic sulfur compounds for growth can be measured by the Sulfur Bioavailability Assay. This assay is based on the fact that all life requires some sulfur for growth and, therefore, a situation can be created whereby quantifying bacterial growth provides a measure of the utilization of any organic or inorganic compound as a source of sulfur. In practice, growth media containing a carbon source at 20 mM is used unamended, amended with 20 mM $Na_2SO_4$, and amended with 20 mM of an organosulfur compound or an inorganic sulfur compound. Each of the three conditions are then inoculated with a microbial culture at $10^5$ microorganisms/mL and incubated for 2 to 5 days with shaking at temperatures appropriate for the microorganism being tested. Bacterial growth is monitored turbidimetrically or by determining colony forming units. The unamended sample serves as a negative control while the sample amended with sulfate serves as a positive control, and both controls are used to assess whether bacterial growth occurred at the expense of sulfur obtained from the organosulfur test compound.

Development of the sulfur-specific culture may be accelerated by mutagenesis by exposure to 1-methyl-3-nitro-1-nitrosoguanidine (NTG) or to ultraviolet irradiation. Mutagenesis with NTG may be performed by spreading a solution of bacteria on an agar plate and placing a crystal of NTG in the center of the plate. During incubation, the NTG crystal dissolves in the agar forming a diffusional concentration gradient which results in no bacterial growth at the center and healthy growth at the outer perimeter of the plate. Between these extremes, a narrow zone of intermediate growth is readily observable and mutagenized bacteria are obtained from this zone. Bacteria for UV-mutagenesis may be pelleted from liquid culture by centrifugation, washed with the above growth media, and resuspended in a volume of the above growth media. Three milliliter portions may be placed in uncovered sterile petri dishes and exposed to doses of UV irradiation sufficient to cause 2 logs of killing, typically 10 $J/m^2$.

A mixed bacterial culture obtained from the selectostats after several months operation was shown to be capable of utilizing a range of organosulfur compounds as the sole source of sulfur as determined by the Sulfur Bioavailability Assay described above. Specific C-S bond cleavage in dibenzothiophene by this mixed culture was demonstrated by gas chromatographic/mass spectrometric analysis. Standard microbiological techniques were used to obtain pure cultures representative of each bacterial type present in the mixed culture. Each pure culture was individually tested for its ability to utilize organosulfur compounds as the sole source of sulfur by the Sulfur Bioavailability Assay An isolated culture which exhibited the ability to utilize organosulfur compounds as the sole source of sulfur in the presence of a nutritional cross-feeding helper culture was the mutant organic sulfur selective microorganism which has been identified as *Bacillus sphaericus*. This *Bacillus sphaericus* strain has been deposited with American Type Culture Collection and assigned number ATCC 53969. The strain is characterized by gram positive short rods of about 0.5μ length, producing beige-/white-colored colonies on nutrient agar and having high organic sulfur specificity by cleavage of C-S bonding.

*Bacillus sphaericus* ATCC No. 53969 does not grow in chemically defined mineral salts medium in the presence of assimilable carbon and an organosulfur compound having sulfur present only in C-S bonding without the presence of a nutritional helper culture providing cross-feeding necessary for growth. Any bacteria providing nutrients for growth under such conditions are satisfactory. Suitable nutritional helper cultures providing completion of elements of nutrition for growth of *Bacillus sphaericus* ATCC No. 53969 may be readily ascertained by one skilled in the art. Presently known suitable helper cultures include several Enterobacter species, such as *E. aerogenes*, *E. agglomerans*, and *E. cloacae*, and a Klebsiella species. The helper culture has no ability to specifically desulfurize organic sulfur compounds.

To confirm the species identity, membrane lipids of the *Bacillus sphaericus* ATCC 53969 were solvent extracted, derivatized and analyzed by gas chromatography. The chromatogram was compared with lipid analyses of known Bacillus cultures recorded in a computer library supplied by Microcheck, Inc. (Northfield, Vt.). These tests identify ATCC 53969 as *Bacillus sphaericus* as shown by Table 1 showing all fatty acids found in the extract compared with the library entry listed in elution order in the left column. An "x" is printed for each acid on the line opposite the fatty acid name indicating the amount of that acid and the library entry mean value for the acid identified with a "+". In cases where the library mean percentage and the actual percentage in the extract are the same an "*" is printed. A dashed line gives a +2 or −2 standard deviation window around the mean value for the library entry. Examination of Table 1 shows high certainty in the identification of the *Bacillus sphaericus*.

TABLE 1

Membrane Lipid Analysis of *Bacillus sphaericus* ATCC No. 53969

| Lipid Type | Percentage 0–65 |
|---|---|
| 14:0 ISO | –X+– |
| 14:0 | +-X |
| 15:0 ISO | ················+················X- |
| 15:0 ANIEISO | —X+— |
| 15:0 | X+- |
| 16:1 ISO E | X —+— |
| 16:0 ISO | X ··········+·········· |
| 16:1 A | -+X- |
| 16:0 | -+X |
| 17:1 ISO E | -+-X |
| 17:0 ISO | –X-+— |
| 17:0 ANIEISO | -X-+— |
| SUMMED FEATURE 5 | -+X- |

*Bacillus sphaericus* ATCC 53969 was compared with other Bacillus species obtained from American Type Culture Collection with respect to carbon sources which would support the growth of these cultures. The cultures were streaked onto the specified agar plates containing the indicated carbon sources and/or inoculated into liquid medium and evaluated after incubating the cultures for 96 hours at 30° C. The results of carbon source utilization studies using a variety of Bacillus strains are shown in Table 2. Carbon source utilization data obtained with *Bacillus sphaericus* ATCC 53969 is identical to that obtained with *Bacillus sphaericus*

ATCC 14577. However, a chemically defined growth medium has not been found in which *Bacillus sphaericus* ATCC 53969 will grow as a pure culture.

pounds with the *Bacillus sphaericus* ATCC 53969 and/or its derivatives in an aqueous growth medium comprising suitable mineral nutrients, an assimilable source

TABLE 2

| Bacillus strains | ATCC # | Glycerol | Sucrose | Citrate | Benzoate | Acetate | Glucose | Ethanol | Succinate | Isobutanol |
|---|---|---|---|---|---|---|---|---|---|---|
| B. subtilis | 33608 | − | − | − | − | − | + | − | − | − |
| B. sphaericus | 14577 | − | − | − | − | − | − | − | − | − |
| B. sphaericus | 53969 | − | − | − | − | − | − | − | − | − |

Additional microbiological tests, including growth on nutrient agar, microscopic observation and growth temperature studies yield identical results with both *B. sphaericus* 14577 and *B. sphaericus* 53969. These data, in conjunction with membrane lipid analysis data, indicate that the microorganism ATCC 53969 is a *Bacillus sphaericus* microorganism.

The Bacillus species listed in Table 2 were evaluated using the above described sulfur bioavailability assay to determine their ability to utilize organically bound sulfur in DBT. Most strains were tested several times using a variety of substrates. The ATCC 53969 strain was the only Bacillus species tested having the C-S bond cleavage property. *Bacillus sphaericus* ATCC No. 53969 was grown in the presence of *Enterobacter aerogenes* or *Enterobacter agglomerans* as a nutrient helper culture. This desulfurization trait in *Bacillus sphaericus* ATCC 53969 has been observed to be stable throughout numerous subculturing events on both selective and non-selective medium.

The *Bacillus sphaericus* ATCC 53969 when grown with a helper culture in chemically defined mineral salts medium, with DBT serving as the sole source of sulfur, results in approximately 0.2 mM 2-hydroxybiphenyl detected in the medium. 2-hydroxybiphenyl is the only metabolite of DBT that has been detected under these conditions.

*Bacillus sphaericus* ATCC 53969 derivatives retain the same or better selective desulfurization trait of the ATCC 53969 strain. *Bacillus sphaericus* ATCC 53969 derivatives having the same selective desulfurization trait are suitable for use in any of the described desulfurization processes and are intended to be included for such uses.

The desulfurization trait of *Bacillus sphaericus* ATCC 53969 is apparently associated with the outer surface of this microorganism. This fact is supported by the observation that the helper culture, as a pure culture, has no ability to grow in chemically defined mineral salts medium in which DBT serves as the sole sulfur source. However, when a desulfurization competent microorganism, specifically *Bacillus sphaericus* ATCC 53969, is simultaneously present, this helper culture grows profusely. This profuse growth of the helper culture could only occur if sulfur liberated from DBT by *Bacillus sphaericus* ATCC 53969 was made available for use by the helper culture.

*Bacillus sphaericus* ATCC 53969 and its derivatives may be used for the highly efficient removal of organic sulfur from organic sulfur-containing carbonaceous materials, particularly naturally occurring fossil fuels such as coal, petroleum, shale, oil, lignite, and synthetic fuels derived therefrom. The organic sulfur may be selectively removed from such materials by contacting with *Bacillus sphaericus* ATCC 53969 and/or its derivatives in an aqueous media at temperatures up to about 42° C. The organic sulfur removal from such materials may be obtained by selective metabolism of the organic sulfur from the solid organic sulfur-containing compounds with the *Bacillus sphaericus* ATCC 53969 and/or its derivatives in an aqueous growth medium comprising suitable mineral nutrients, an assimilable source of carbon, and a nutritional helper culture providing necessary elements of nutrition for growth of the *Bacillus sphaericus*. The metabolism is under aerobic conditions requiring oxygen with the pH of the aqueous growth media maintained at about a pH of 5 to 8 and preferably about 6 to 7, and a temperature of about 15° to 34° C., preferably about 28° to 32° C. The higher temperature ranges result in faster metabolism, however, the microorganisms are known to not tolerate temperatures in the order of 42° C. The aqueous media should contain a suitable concentration of microorganisms to achieve the desired selective sulfur removal within the desired time interval.

I have found that *Bacillus sphaericus* ATCC 53969 and its derivatives uniquely metabolize sulfur by cleavage of the C-S bonding in organic carbonaceous materials; for example, in the metabolism of dibenzothiophene, the sole products are 2-hydroxybiphenyl and inorganic sulfate. These properties of the microorganism metabolism render *Bacillus sphaericus* ATCC 53969 and its derivatives a specific agent for use in organic chemical synthesis for cleavage of organic C-S bonding which may be used in various organic process synthesis systems. Likewise, the unique properties of *Bacillus sphaericus* ATCC 53969 and its derivatives may be utilized in desulfurizing degradation of a wide variety of organic materials by cleavage of organic C-S bonding in recycling operations, such as in breakdown of sulfur containing organic molecules such as in rubber products.

The microbiological process of this invention results in the conversion of organic sulfur to inorganic sulfate. Sulfur in the form of organically bound sulfur presents very difficult separation, while the inorganic sulfate produced by this process may be easily removed by a wide variety of methods readily apparent to one of ordinary skill in the art.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

I claim:

1. A process for reducing the sulfur content of sulfur-containing organic carbonaceous material comprising, contacting a sulfur-containing organic carbonaceous material with microorganism *Bacillus sphaericus* strain ATCC No. 53969.

2. A process according to claim 1 wherein said carbonaceous material is coal.

3. A process according to claim 1 wherein said carbonaceous material is hydrocarbon oil.

4. A process according to claim 1 wherein said microorganism metabolizes said sulfur-containing organic carbonaceous material by cleavage of organic C-S bonds and production of inorganic sulfate when grown in a growth medium comprising mineral nutrients and an assimilable source of carbon in the substantial absence of a sulfur-containing compound except said sulfur-containing organic carbonaceous material, and in the presence of a nutritional helper culture providing completion of elements of nutrition for growth of said *Bacillus sphaericus* and in the presence of oxygen at temperatures about 20° to about 34° C.

5. A process according to claim 4 wherein the pH is maintained at about 6 to about 7.

6. A process according to claim 5 wherein the temperature is maintained at about 30° to about 32° C.

7. A process according to claim 4 wherein the temperature is maintained at about 30° to about 32° C.

8. A process according to claim 4 wherein said nutritional helper culture is bacteria selected from the species consisting of Enterobacter and Klebsiella.

9. A process according to claim 4 wherein said carbonaceous material is coal.

10. A process according to claim 4 wherein said carbonaceous material is hydrocarbon oil.

11. A process for cleavage of organic C-S bonds comprising, contacting an organic carbonaceous material having C-S bonds with microorganism *Bacillus sphaericus* strain ATCC No. 53969.

12. A process according to claim 11 wherein said organic carbonaceous material is a component in an organic synthesis process.

13. A process according to claim 11 wherein said organic material is a component in a recycling process.

14. A process according to claim 11 wherein said microorganism metabolizes said sulfur-containing organic carbonaceous material by cleavage of organic C-S bonds and production of inorganic sulfate when grown in a growth medium comprising mineral nutrients and an assimilable source of carbon in the substantial absence of a sulfur-containing compound except said sulfur-containing organic carbonaceous material, and in the presence of a nutritional helper culture providing completion of elements of nutrition for growth of said *Bacillus sphaericus* and in the presence of oxygen at temperatures about 20° to about 34° C.

15. A process according to claim 14 wherein the pH is maintained at about 6 to about 7.

16. A process according to claim 15 wherein the temperature is maintained at about 30° to about 32° C.

17. A process according to claim 14 wherein the temperature is maintained at about 30° to about 32° C.

18. A process according to claim 14 wherein said nutritional helper culture is bacteria selected from the species consisting of Enterobacter and Klebsiella.

19. A process according to claim 14 wherein said carbonaceous material is coal.

20. A process according to claim 14 wherein said carbonaceous material is hydrocarbon oil.

21. A process for cleavage of organic C-S bonds comprising, contacting an organic carbonaceous material having C-S bonds with organic sulfur selective derivative microorganisms of *Bacillus sphaericus* strain ATCC 53969, which selectively reduces the sulfur content of sulfur-containing organic carbonaceous material by cleavage of organic C-S bonds in a growth medium comprising mineral nutrients and an assimilable source of carbon in the substantial absence of a sulfur-containing compound except said sulfur-containing organic carbonaceous material, and in the presence of a nutritional helper culture providing completion of elements of nutrition for growth of said microorganisms and in the presence of oxygen at temperatures about 20° to about 34° C.

22. A process for reducing sulfur content of sulfur-containing organic carbonaceous material comprising, contacting a sulfur-containing organic carbonaceous material with organic sulfur selective derivative microorganisms of *Bacillus sphaericus* strain ATCC 53969, which selectively reduces the sulfur content of sulfur-containing organic carbonaceous material by cleavage of organic C-S bonds in a growth medium comprising mineral nutrients and an assimilable source of carbon in the substantial absence of a sulfur-containing compound except said sulfur-containing organic carbonaceous material, and in the presence of a nutritional helper culture providing completion of elements of nutrition for growth of said microorganisms and in the presence of oxygen at temperatures about 20° to about 34° C.

* * * * *

UNITED STATES PATENT AND TRADEMARK OFFICE
CERTIFICATE OF CORRECTION

PATENT NO. : 5,198,341
DATED      : March 30, 1993
INVENTOR(S): John J. Kilbane, II It is certified that error appears in the above-identified patent and that said Letters Patent is hereby corrected as shown below:

On the title page, item (54): Title should read--

--BACILLUS SPHAERICUS MICROORGANISM USEFUL FOR CLEAVAGE OF ORGANIC C-S BONDS--

Signed and Sealed this

Thirtieth Day of November, 1993

Attest:

BRUCE LEHMAN

*Attesting Officer*

*Commissioner of Patents and Trademarks*